United States Patent
Guan et al.

(10) Patent No.: US 11,085,075 B2
(45) Date of Patent: Aug. 10, 2021

(54) DNA BARCODING PRIMER FOR IDENTIFYING CEPHALOPODA AND USE THEREOF

(71) Applicant: China Jiliang University, Hangzhou (CN)

(72) Inventors: Feng Guan, Hangzhou (CN); Jin Zhao, Hangzhou (CN)

(73) Assignee: CHINA JILIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/931,082

(22) Filed: May 13, 2020

(65) Prior Publication Data

US 2020/0362389 A1 Nov. 19, 2020

(30) Foreign Application Priority Data

May 14, 2019 (CN) .......................... 201910400136.4

(51) Int. Cl.
  *C12Q 1/68* (2018.01)
  *C12Q 1/686* (2018.01)
  *C12Q 1/6888* (2018.01)

(52) U.S. Cl.
  CPC ........... *C12Q 1/686* (2013.01); *C12Q 1/6888* (2013.01); *C12Q 2565/537* (2013.01)

(58) Field of Classification Search
  CPC ...................................................... C12Q 1/68
  See application file for complete search history.

(56) References Cited

FOREIGN PATENT DOCUMENTS

| CN | 105506103 A | * | 4/2016 |
| CN | 107974507 A | * | 5/2018 |

* cited by examiner

*Primary Examiner* — Aaron A Priest
(74) *Attorney, Agent, or Firm* — Flener IP & Business Law; Zareefa B Flener

(57) ABSTRACT

The present invention provides a DNA barcode and method for identifying cuttlefishes, mainly depending on the diversity of mitochondrial DNA, including designing universal primers on conservative regions on both sides of the species-specific variable region, amplifying DNA from cuttlefishes, and sequencing PCR products to obtain DNA sequences, and identifying cuttlefish species based on the similarity by comparing with the species information in the database. The method is advantageous in that it can achieve efficient and specific amplification of DNA from such cephalopods as cuttlefishes, with low requirements for necessary instruments and simple operation processes. In addition, the method can be carried out in most molecular biology laboratories, which greatly improves the probability of success of molecular identification for cuttlefishes and sibling species thereof.

2 Claims, 1 Drawing Sheet

Specification includes a Sequence Listing.

DNA BARCODING PRIMER FOR IDENTIFYING CEPHALOPODA AND USE THEREOF

TECHNICAL FIELD

The present invention belongs to the technical field of marine organism identification, and particularly relates to a DNA barcoding primer for identifying cephalopods and a use method thereof, i.e., a DNA barcoding method for identifying cuttlefishes and sibling species thereof.

BACKGROUND

The DNA barcoding identification technique is mainly used for species identification by using relatively short DNA fragments in the organism with sufficient variation that can represent and map this species by means of PCR amplification, sequencing and alignment, etc. DNA barcoding techniques were developed by a Canadian scientist Hebert in 2003. After screening, the COI gene of mitochondrial DNA (mtDNA) for animal identification was identified as a barcoding target for species identification. Since then, the gene has shown good discrimination in the identification of many animals, especially in the fish identification, biodiversity research and wild animal identification, and identification of adulterated food of animal source. At present, DNA barcoding has become an important tool in the field of biological researches, which plays a significant role in species identification, evolutionary traceability and ecological researches. Meanwhile, DNA barcoding techniques have also been continuously developed with the development of bioinformatics and computational biology. Studies have shown that the techniques can identify 90% of common animal species and 93-98% of common fishes, after which the DNA amplification rate of common fishes can reach 100% through primer design and tailing optimization. In the development of DNA barcoding techniques, COIII gene and Cytb gene are also regarded as detection targets, which in combination with DNA barcoding database (http://www-.barcodinglife.org) and GenBank database (http://blast.ncbi.nlm.nih.gov/ Blast.cgi) can identify most species. However, on the other hand, DNA barcoding techniques also have deficiencies and need to be continuously improved and developed. The key is to find a gene sequence that can distinguish closely related species and design primers with good universality and high-efficiency amplification performance. Some researchers have pointed out that the COI gene has certain problems as a DNA barcode in highly-conserved species or animals that have evolved slowly and some genes have double copies. Even common primers cannot be amplified for certain species or cannot be identified due to the high sequence identity. 16S rRNA and 18S rRNA gene sequences are required as a supplement to DNA barcoding technique. It has been suggested that the 16S rRNA gene sequence is more abundant in terms of interspecific variation than the COI gene. Other studies have indicated that the 16S rRNA gene of lower aquatic animals is more suitable for use as a DNA barcode than the COI gene. Therefore, in the practical application, it is of necessity to select suitable primers and optimize them for the process of identifying species with barcoding.

Among cephalopods, cuttlefish, octopus, and squid are important economic marine animals, and are also lower marine animals. Their diverse variety and morphology make it difficult for identification and classification researches. There are even two different names *Sepiella maindroni* (common Chinese cuttlefish) and *Sepiella japonica* (Japanese spineless cuttlefish) had been verified the same species. Due to the lack of in-depth classification researches, morphological identification is still an important means of cephalopod species identification, but morphological identification techniques are severely limited in the identification of dismembered and processed products. On the other hand, cephalopods are significantly different from common fishes due to the complex arrangement and recombination of mitochondrial DNA and the existence of non-coding sequences, and the commonly used DNA barcodes cannot meet requirements of the identification of these species, which is mainly due to the fact that existing DNA barcoding primers cannot normally amplify DNA of some cuttlefishes and their closely related species. At present, DNA analysis-based cuttlefish identification methods mainly include DNA sequencing and PCR-RFLP combined technology, nuclear genome markers and mitochondrial genes (COI and 16S rDNA) joint identification, and multiple mitochondrial gene marker (COI, 12S rDNA, CytB and ATP6) probes and fluorescent quantitative PCR combined technology, etc. Such DNA analysis techniques are more complicated in procedures, lower in universality, and higher in instrument requirements as compared to DNA barcoding techniques. In order to screen DNA barcoding sequences suitable for the identification of cephalopods, especially cuttlefishes, the present invention screens the mitochondrial gene sequences of common cuttlefish species and optimizes the design detection system, and discloses a DNA barcoding primer more suitable for cuttlefish identification and a detection system thereof. The detection system is advantageous for the identification of processed cuttlefish and squid products.

SUMMARY

The present invention provides a DNA barcoding-based PCR amplification primer, which is capable of specifically and effectively amplifying DNA of molluscs such cephalopods as cuttlefish, octopus, and squid. The amplified products are subjected to sequencing and sequence alignment so as to achieve species identification.

The present invention provides a PCR primer for amplifying products of different cephalopods between 620 bp and 680 bp, without cross-reaction with DNA of common meat animals and fishes. The present invention solves the problem that the existing DNA barcode cannot amplify DNA of some cuttlefishes. The present invention does not require practitioners' morphological identification experience, which makes up for the shortcomings of the existing morphological identification methods and DNA barcoding techniques for the identification of cephalopod cuttlefish species.

The present invention provides a DNA barcoding primer pair for identifying such cephalopods as cuttlefish, octopus and squid, including an upstream primer with a sequence as shown in SEQ ID NO: 1 and a downstream primer with a sequence as shown in SEQ ID NO: 2.

The upstream sequence SEQ ID NO: 1 is as follows:

5'-AACAAGAGCGACGGGCGATA-3'.

The downstream sequence SEQ ID NO: 2 is as follows:

5'-TGTGCCAGCATCTGCGGTTA-3'.

The DNA barcode is a PCR amplification and sequencing primer. The primer can perform PCR amplification and sequencing on DNA sequence fragments of cephalopods.

The DNA barcode can also be optimized as another PCR amplification and sequencing primer, including an upstream primer and a downstream primer. The sequence information is as follows:

```
the upstream sequence SEQ ID NO: 3:
5'-AACAAGAGTGACGGGCGATA-3',
and the downstream sequence SEQ ID NO: 4:
5'-TGTGCCAGCATCCGCGGTTA-3'.
```

The DNA barcode as described above can also be further optimized as another PCR amplification primer, including an upstream primer and a downstream primer. The sequence information is as follows:

```
the upstream sequence SEQ ID NO: 5:
5'-TGTAAAACGACGGCCAGTAACAAGAGYGACGGGCGATA-3',
and the downstream sequence SEQ ID NO: 6:
5'-CAGGAAACAGCTATGACTGTGCCAGCATCYGCGGTTA-3'.
```

The sequencing primers corresponding to the amplification products of SEQ ID NO: 5 and SEQ ID NO: 6 have sequences of M13F and M13R, respectively:

```
the upstream sequence M13F:
                                    (SEQ ID NO: 7)
5'-TGTAAAACGACGGCCAGT-3',
and the downstream sequence M13R:
                                    (SEQ ID NO: 8)
5'-CAGGAAACAGCTATGAC-3'.
```

The present invention also provides a PCR method for such cephalopods as cuttlefish, octopus and squid, i.e., using the above primer pair for amplification and detection, comprising the following specific steps of:

1) extracting DNA of an individual to be identified for further use;

2) preparing a PCR amplification system, including a PCR buffer at an appropriate concentration, dNTP, $Mg^{2+}$ ion, Taq DNA polymerase, a sample DNA template with a total amount of not less than 40 ng, upstream and downstream primers and double distilled water; where the PCR amplification of primers SEQ ID NO: 1 and SEQ ID NO: 2 is as follows: denatured at 95° C. for 5 min, denatured at 95° C. for 30 s, annealed at 52.5° C. for 35 s, and extended at 72° C. for 40 s for one cycle, 30 cycles in total; then maintained at 72° C. for 5 min, and cooled to 4° C. at last;

the same procedure applies to primer pairs SEQ ID NO: 3 and SEQ ID NO: 4, and SEQ ID NO: 5 and SEQ ID NO: 6, and the annealing temperature can be changed to 50° C. and 52° C., respectively;

3) detecting the size of PCR products, where PCR products of SEQ ID NO: 1 and SEQ ID NO: 2 have the same product size as those of SEQ ID NO: 3 and SEQ ID NO: 4, and the PCR products are between 620 bp-640 bp in size; and PCR products obtained from the primer pair of SEQ ID NO: 5 and SEQ ID NO: 6 are between 650 bp-680 bp in size;

4) sequencing the PCR products amplified by the combination of the primers of SEQ ID NO: 1 and SEQ ID NO: 2 with SEQ ID NO: 3 and SEQ ID NO: 4 as described in step 3 above with corresponding PCR primers; and sequencing the PCR products obtained from the primers of SEQ ID NO: 5 and SEQ ID NO: 6 by using primers M13F and M13R; and 5) calibrating or editing the resulting sequence, and then submitting the sequence to the GenBank database (http://blast.ncbi.nlm.nih.gov/Blast.cgi) for alignment, and confirming the species based on the similarity.

Compared with the existing morphological identification method, the method of the present invention is not affected by the experience of inspectors or the morphological changes after processing, which greatly improves the feasibility of sample detection. Compared with the existing DNA barcoding techniques, the technology platform used is completely the same, but more importantly, the present invention solves the problem of false negatives caused by the difficulty in amplifying DNA of some cephalopods by the existing DNA barcode. Therefore, the DNA barcode and its application method established by the present invention are important supplement to the existing DNA barcoding techniques, and can be used to identify cuttlefishes and closely related species.

DETAILED DESCRIPTION

The applicants were engaged in the traceability identification process of domestic animals (pig, cattle, sheep) and marine fishes and processed foods. After screening and optimizing the existing DNA barcoding primers, it was found that the existing DNA barcoding primers somehow fail to amplify DNA samples of some cuttlefishes and squids. The PCR products of these cuttlefish DNA samples cannot be obtained by changing or optimizing the PCR system or condition of the existing primers. In order to solve this problem, the applicants reviewed and compared the mitochondrial DNA sequences of kisslip cuttlefish, swordtip squid, golden cuttlefish, common Chinese cuttlefish, pharaoh cuttlefish, and sibling species squid and octopus, used the mitochondrial DNA of large yellow croaker, little yellow croaker, belt fish, cattle, sheep, and chicken as control, and compared and analyzed sequences within the specific COI, 12S rRNA, and 16S rRNA regions. The applicants have found a diversified sequence of cuttlefish, squid and octopus, and designed primers based on the conservative regions at both flanks of this sequence, and optimized the PCR conditions for these primers. After sequencing the amplified products, species can be identified based on the similarity by means of sequence alignment.

The present invention is specifically illustrated through specific embodiments as follows. The present invention is further described by processes and operations in the following examples, which are not intended to limit the present invention by any means. The molecular biology techniques or steps adopted in the examples can achieve the same effect by using similar products or referring to Molecular Cloning.

EXAMPLE 1

Figure 1:
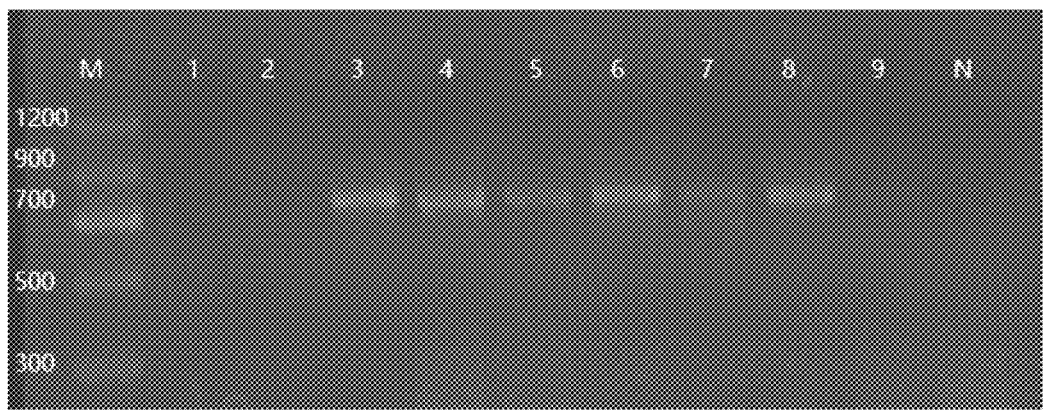
FIG. 1: Existing COI primers (Group III in Table 2) are difficult to amplify DNA of some cuttlefishes, where M is the molecular weight standard; Lanes 1-2 represent kisslip cuttlefish and swordtip squid, Lanes 7-9 represent large yellow croaker, little yellow croaker, golden cuttlefish, common Chinese cuttlefish, pharaoh cuttlefish, and shredded squid; and N is a negative control.

There is a Mismatch Between the DNA Barcoding Primer and DNA Sequences of Some Cuttlefishes, Leading to Hindered PCR Amplification In view of many reports on the identification of fishes with DNA barcodes, fishes with a low price being pretended to be high-price fishes with similar morphology have been found in fishes and their processed products and even customs import quarantine. There are also many reports of similar events in processed products, the ratio of adulterations may be up to 40% or more. During the process of detecting fishes and processed products commercially available in Zhejiang, as a province of abundant marine resources in China, we have optimized and screened DNA barcoding primers (WANG Ping-Ya, HUANG Zhu-Liang, JIN Yu-Ting, TANG Hai-Feng, SUN Ying, ZHAO Jin, GUAN Feng. Optimization and selection of 4 fish DNA barcoding primer sets, Journal of Food Safety and Quality, 2018, 9(16): 4387-4392). It has been found that the current DNA barcoding primers have difficulties in amplifying DNA of certain varieties of cuttlefish, such as kisslip cuttlefish and swordtip squid (FIG. 1). Then the mitochondrial DNA (mtDNA) sequences of common cuttlefishes (as shown in Table 1) were reviewed, and the pairing specificity of the primer sequence (as shown in Table 2) and cuttlefish DNA were analyzed.

TABLE 1

Mitochondrial DNA sequence of cuttlefishes

| Cuttlefish species | English name | Accession No. | Length (bp) |
|---|---|---|---|
| Sepia esculenta | Golden cuttlefish | AB266516 | 16199 |
| Loliolus beka | Beka squid | KT254309 | 17483 |
| Sepiella maindroni | Common Chinese cuttlefish | KR912215 | 16170 |
| Sepia pharaonis | Pharaoh cuttlefish | AP013076 | 16203 |
| Sepia lycidas | Kisslip cuttlefish | KF690633 | 16219 |
| Uroteuthis edulis | Swordtip squid | AB675080 | 17360 |
| Octopodidae | Octopus | KT581981 | 16084 |

With regard to common DNA barcoding primers listed in Table 2, 3 sets of primers are COI gene primers, and others are 12S rRNA and 16S rRNA gene primers. The results of specificity analysis suggested that the two upstream primers in the common fish primer sets (group I and group III, both of which have the same specific binding sequence) had C-A mismatches (swordtip squid, common Chinese cuttlefish, and squid) and C-T mismatches (kisslip cuttlefish and octopus) with different species of cuttlefishes at the −3 position, respectively. Depending on the species, there were 3-4 mismatched bases in the upstream primers. The downstream primer FishR1 also had an A-G mismatch with golden cuttlefish DNA sequence at the −3 position. FishR2 had a C-T mismatch with DNA sequences of five test cuttlefishes and squids as well as octopus at the −3 position. According to the mismatch theory (GUAN Feng, YANG Li-Guo, AI Jun-Tao, LIU Shou-Ren, SHI Guo-Qing. Development of a rapid mismatch PCR method using tetra-primer ARMS for detection of BMPR-IB gene mutation in sheep, HEREDI- TAS, 2005, 27(4): 579-583), C-A is a weak mismatch, A-G and C-T are strong mismatches, add to other mismatched bases in the primer, which is enough to block the PCR amplification reaction. Therefore, it is speculated that the existence of mismatch is the main reason for difficulty in obtaining PCR products normally. Group II COI primers LC01490 and HCO2198 are mainly designed for lower animals. Specificity analysis showed that the upstream primer LC01490 completely matched with 10 bases at the 3' end of the DNA sequences of 5 species of cuttlefishes and squids as well as octopus, which could generate effective base pairing. However, the downstream primers HCO2198 and FishR1 also had A-G mismatches with the golden cuttlefish DNA sequence at the −3 position. The 12S rRNA and 16S rRNA gene primers also had the problem of multiple base mismatches with the cuttlefish DNA sequence, which is prone to false negative results without PCR products due to mismatches. Therefore, the above-mentioned common DNA barcoding primers have certain deficiencies in the identification of cuttlefishes, are prone to false negatives in the detection, and are also difficult to form a unified standard for the actual detection. There is a need for optimizing or finding new DNA barcoding primers.

TABLE 2

Names and sequences of common DNA barcoding primers

| Primers | Name | Primer sequence (5'-3') |
|---|---|---|
| Group I (COI gene) | FishF1 | TCAACCAACCACAAAGACATTGGCAC (SEQ ID NO: 9) |
| | FisHR1 | TAGACTTCTGGGTGGCCAAAGAATCA (SEQ ID NO: 10) |
| | FishF2 | TCGACTAATCATAAAGATATCGGCAC (SEQ ID NO: 11) |
| | FishR2 | ACTTCAGGGTGACCGAAGAATCAGAA (SEQ ID NO: 12) |
| Group II (COI gene) | LCO1490 | GGTCAACAAATCATAAAGATATTGG (SEQ ID NO: 13) |
| | HCO2198 | TAAACTTCAGGGTGACCAAAAAATCA (SEQ ID NO:14) |
| Group III (COI gene) | FishF2-t1 | TGTAAAACGACGGCCAGTCGACTAATC ATAAAGATATCGGCAC (SEQ ID NO: 15) |
| | VF2-t1 | TGTAAAACGACGGCCAGTCAACCAACC ACAAAGACATTGGCAC (SEQ ID NO: 16) |
| | FishR2-t1 | CAGGAAACAGCTATGACACTTCAGGGT GACCGAAGAATCAGAA (SEQ ID NO: 17) |
| | FR1d-t1 | CAGGAAACAGCTATGACACCTCAGGGT GTCCGAARAAYCARAA (SEQ ID NO: 18) |
| 12S rRNA | 12SA | AAACTGGGATTAGATACCCCACTAT (SEQ ID NO: 19) |
| | 12SB | GAGAGTGACGGGCGGTGTGT (SEQ ID NO: 20) |
| 16S rRNA | 16sarL | CGCCTGTTTACCAAAAACAT (SEQ ID NO: 21) |
| | 16sbrH | CCGGTCTGAACTCAGATCACGT (SEQ ID NO: 22) |

Note:
The bold letters in Group III primers represent the tailed primer portion, i.e. the sequencing primer of M13.

EXAMPLE 2

Design and Optimization of Cuttlefish DNA Barcoding Primers

In order to solve the problem found in Example 1, the applicants searched the NCBI database for mitochondrial DNA sequences of common cuttlefish species (Table 1), and used mitochondrial DNA of closely related species squid and octopus and common meat sources of large yellow croaker, little yellow croaker, belt fish, pig, cattle, sheep, chicken and duck as controls. Through sequence alignment, base difference and substitution rate analysis, a DNA sequence in the 12S rRNA gene region of cuttlefish was used as the DNA barcode for species identification. Three sets of primers were designed for the conservative regions on both sides of this sequence. See Table 3 for the primers.

TABLE 3

Cuttlefish DNA barcoding primers

| Groups | Name of Primer | Primer sequence (5'-3') |
|---|---|---|
| Group 1 | Wuzei12SF1 | AACAAGAGCGACGGGCGATA (SEQ ID NO: 1) |
| | Wuzei12SR1 | TGTGCCAGCATCTGCGGTTA (SEQ ID NO: 2) |
| Group 2 | Wuzei12SF2 | AACAAGAGTGACGGGCGATA (SEQ ID NO: 3) |
| | Wuzei12SR2 | TGTGCCAGCATCCGCGGTTA (SEQ ID NO: 4) |
| Group 3 | Wuzei12SF3 | TGTAAAACGACGGCCAGTAA CAAGAGYGACGGGCGATA (SEQ ID NO: 5) |
| | Wuzei12SR3 | CAGGAAACAGCTATGACTGT GCCAGCATCYGCGGTTA (SEQ ID NO: 6) |
| Sequencing group | M13F | TGTAAAACGACGGCCAGT (SEQ ID NO: 7) |
| | M13R | CAGGAAACAGCTATGAC (SEQ ID NO: 8) |

It should be noted that the primer in Group 1 is a universal primer, and the primers in Groups 2 and 3 are alternative optimized primers. The DNA templates used for the above primer tests included DNA from common Chinese cuttlefish, golden cuttlefish, swordtip squid, pharaoh cuttlefish, and kisslip cuttlefish, as well as squid, large yellow croaker, little yellow croaker, belt fish, pig, cattle, sheep, chicken and duck.

20 µL of PCR reaction system contained (Buffer with 2.0 mM MgSO$_4$) 10×Buffer 2 µL, 1 set of upstream and downstream primers 1 µL (10 µM) each, dNTPs 1.6 µL (25 mM), Taq Polymerase 0.2 µL (Thermofisher product, 5 U/µL), DNA mixed template (DNA mix of 3 species of cuttlefishes) 3 µL (about 30 ng), making up to 20 µL with ultrapure water.

The PCR program was as follows: pre-denatured at 95° C. for 5 min; 30 cycles (denatured at 95° C. for 30 s, annealed at a gradient temperature of 48° C.-62° C. for 30 s, extended at 72° C. for 30 s); extended at 72° C. for 5 min at the end of the cycle reaction, cooled to and stored at 4° C. After subjecting PCR products to 2% agarose electrophoresis (4S Red staining) detection, the optimized PCR program was fixed according to the brightness and size of the bands. The final annealing temperatures of the three sets of primers were 52° C.-58° C., 51° C.-58° C. and 56° C.-61° C., respectively.

The further test results showed that the optimal temperature of the three sets of primers were 52.5° C., 52° C. and 58° C., respectively. The optimized primers were tested for versatility and specificity according to the optimal annealing temperature and PCR reaction system. The versatility results suggested that the three sets of primers have no significant difference in the brightness of the cuttlefish and squid DNA amplification products, all of which could effectively amplify the test DNA. The specificity test suggested that the three sets of primers could effectively amplify DNA from 5 tested cuttlefishes and 4 tested squids, and there was no cross-reaction with DNA from large yellow croaker, little yellow croaker, belt fish, pig, cattle, sheep, chicken and duck.

EXAMPLE 3

Cuttlefish Species Identification and Analysis

Figure 2:
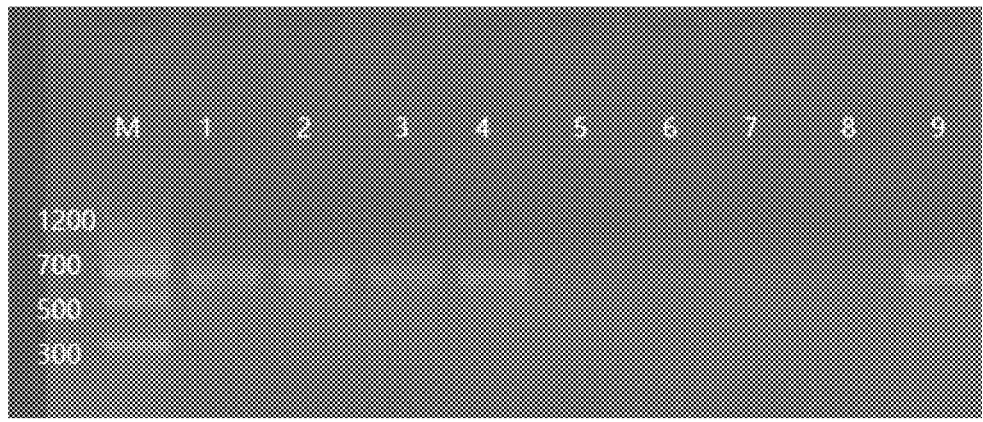
FIG. 2 shows the amplification results of cuttlefish DNA by the primer pair of Wuzei12SF1-Wuzei12SR1 in the present invention, where M is the molecular weight standard; Lanes 1-4 and 9 represent golden cuttlefish, kisslip cuttlefish, swordtip squid, common Chinese cuttlefish and pharaoh cuttlefish respectively; and Lanes 5-8 represent large yellow croaker, little yellow croaker, cattle, and chicken.

The PCR products of common Chinese cuttlefish, golden cuttlefish, swordtip squid, pharaoh cuttlefish, and kisslip cuttlefish amplified by the primer in Group 1 in Example 2 were recovered (FIG. 2), and were sent to HANGZHOU TSINGKE BIO-TECH CO., LTD. for bi-directional direct sequencing.

The sequencing results were viewed by using Chromas and the sequencing results were calibrated in conjunction with DNAstar software package to determine the accuracy of upstream and downstream sequencing. After splicing, they were aligned in NCBI (https://www.ncbi.nlm.nih.gov) database Blast. When the similarity of the alignment results was ≥98%, it was considered that the species was identified. The identification results of the five species of cuttlefishes were shown in Table 4, all of which were matched with the corresponding species sequence accession number. However, the alignment result of the K10F sample showed Common Chinese cuttlefish (KR912215) and Japanese spineless cuttlefish (AB675082), and they had the same similarity. Research data suggested that the two were the same species, but the names are different.

TABLE 4

Identification results of 5 cuttlefish species

| Sample | Corresponding sequence No. | Similarity | English name | Species |
|---|---|---|---|---|
| K1F | AB266516.1 | 99% | Golden cuttlefish | Sepia esculenta |
| K3F | KJ162574.1 | 99% | Kisslip cuttlefish | Sepia lycidas |
| K5F | KT254309.1 | 99% | Beka squid | Loliolus beka |
| K10F | KR912215.1 | 99% | Common Chinese cuttlefish | Sepiella maindroni |
| | AB675082.1 | 99% | Japanese spineless cuttlefish | Sepiella laponica |
| K12F | KC632521 | 98% | Pharaoh cuttlefish | Sepia pharaonis |

The above results suggested that the cuttlefish DNA barcoding system established by the present invention can identify Common Chinese cuttlefish and Japanese spineless cuttlefish as the same species without relevant knowledge background. Therefore, in addition to the basic advantages of the DNA barcode, the present invention can also provide evidences for the morphological identification of cuttlefishes. The cephalopod DNA barcoding system established by the present invention can be used as a supplement to the existing DNA barcode.

What is claimed is:

1. A method for identifying cephalopods, wherein the method comprises subjecting an individual to be detected to PCR amplification by using a DNA barcoding primer pair to produce an amplification product, sequencing the amplification product, calibrating or editing the sequence obtained after amplification and submitting the sequence obtained after calibrating or editing to the GenBank database for alignment, and identifying the species of the individual to be detected based on the similarity of DNA sequences; wherein the sequence of the upstream primer of the DNA barcoding primer pair is as shown in SEQ ID NO: 3, and the sequence of the downstream primer of the DNA barcoding primer pair is as shown in SEQ ID NO: 4.

2. The method according to claim 1, wherein in the PCR amplification, the primer pair is annealed at 50° C.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: artificial sequence
<220> FEATURE:
<223> OTHER INFORMATION: Wuzei12SF1

<400> SEQUENCE: 1
aacaagagcg acgggcgata                                                 20

<210> SEQ ID NO 2
<211> LENGTH: 20
<212> TYPE: DNA
<213> ORGANISM: artificial sequence
<220> FEATURE:
<223> OTHER INFORMATION: Wuzei12SR1

<400> SEQUENCE: 2
tgtgccagca tctgcggtta                                                 20

<210> SEQ ID NO 3
<211> LENGTH: 20
<212> TYPE: DNA
<213> ORGANISM: artificial sequence
<220> FEATURE:
<223> OTHER INFORMATION: Wuzei12SF2

<400> SEQUENCE: 3
aacaagagtg acgggcgata                                                 20

<210> SEQ ID NO 4
<211> LENGTH: 20
<212> TYPE: DNA
<213> ORGANISM: artificial sequence
<220> FEATURE:
<223> OTHER INFORMATION: Wuzei12SR2

<400> SEQUENCE: 4
tgtgccagca tccgcggtta                                                 20

<210> SEQ ID NO 5
<211> LENGTH: 38
<212> TYPE: DNA
<213> ORGANISM: artificial sequence
<220> FEATURE:
<223> OTHER INFORMATION: Wuzei12SF3

<400> SEQUENCE: 5
tgtaaaacga cggccagtaa caagagygac gggcgata                             38

<210> SEQ ID NO 6
<211> LENGTH: 37
<212> TYPE: DNA
<213> ORGANISM: artificial sequence
<220> FEATURE:
<223> OTHER INFORMATION: Wuzei12SR3

<400> SEQUENCE: 6
caggaaacag ctatgactgt gccagcatcy gcggtta                              37

<210> SEQ ID NO 7
<211> LENGTH: 18
<212> TYPE: DNA
<213> ORGANISM: artificial sequence

```
<220> FEATURE:
<223> OTHER INFORMATION: M13F

<400> SEQUENCE: 7
tgtaaaacga cggccagt                                                    18

<210> SEQ ID NO 8
<211> LENGTH: 17
<212> TYPE: DNA
<213> ORGANISM: artificial sequence
<220> FEATURE:
<223> OTHER INFORMATION: M13R

<400> SEQUENCE: 8
caggaaacag ctatgac                                                     17

<210> SEQ ID NO 9
<211> LENGTH: 26
<212> TYPE: DNA
<213> ORGANISM: artificial sequence
<220> FEATURE:
<223> OTHER INFORMATION: FishF1

<400> SEQUENCE: 9
tcaaccaacc acaaagacat tggcac                                           26

<210> SEQ ID NO 10
<211> LENGTH: 26
<212> TYPE: DNA
<213> ORGANISM: artificial sequence
<220> FEATURE:
<223> OTHER INFORMATION: FishR1

<400> SEQUENCE: 10
tagacttctg ggtggccaaa gaatca                                           26

<210> SEQ ID NO 11
<211> LENGTH: 26
<212> TYPE: DNA
<213> ORGANISM: artificial sequence
<220> FEATURE:
<223> OTHER INFORMATION: FishF2

<400> SEQUENCE: 11
tcgactaatc ataagatat cggcac                                            26

<210> SEQ ID NO 12
<211> LENGTH: 26
<212> TYPE: DNA
<213> ORGANISM: artificial sequence
<220> FEATURE:
<223> OTHER INFORMATION: FishR2

<400> SEQUENCE: 12
acttcagggt gaccgaagaa tcagaa                                           26

<210> SEQ ID NO 13
<211> LENGTH: 25
<212> TYPE: DNA
<213> ORGANISM: artificial sequence
<220> FEATURE:
<223> OTHER INFORMATION: LCO1490

<400> SEQUENCE: 13
ggtcaacaaa tcataaagat attgg                                            25
```

<210> SEQ ID NO 14
<211> LENGTH: 26
<212> TYPE: DNA
<213> ORGANISM: artificial sequence
<220> FEATURE:
<223> OTHER INFORMATION: HCO2198

<400> SEQUENCE: 14
taaacttcag ggtgaccaaa aaatca                                              26

<210> SEQ ID NO 15
<211> LENGTH: 43
<212> TYPE: DNA
<213> ORGANISM: artificial sequence
<220> FEATURE:
<223> OTHER INFORMATION: FishF2-t1

<400> SEQUENCE: 15
tgtaaaacga cggccagtcg actaatcata agatatcgg cac                           43

<210> SEQ ID NO 16
<211> LENGTH: 43
<212> TYPE: DNA
<213> ORGANISM: artificial sequence
<220> FEATURE:
<223> OTHER INFORMATION: VF2-t1

<400> SEQUENCE: 16
tgtaaaacga cggccagtca accaaccaca aagacattgg cac                          43

<210> SEQ ID NO 17
<211> LENGTH: 43
<212> TYPE: DNA
<213> ORGANISM: artificial sequence
<220> FEATURE:
<223> OTHER INFORMATION: FishR2-t1

<400> SEQUENCE: 17
caggaaacag ctatgacact tcagggtgac cgaagaatca gaa                          43

<210> SEQ ID NO 18
<211> LENGTH: 43
<212> TYPE: DNA
<213> ORGANISM: artificial sequence
<220> FEATURE:
<223> OTHER INFORMATION: FR1d-t1

<400> SEQUENCE: 18
caggaaacag ctatgacacc tcagggtgtc cgaaraayca raa                          43

<210> SEQ ID NO 19
<211> LENGTH: 25
<212> TYPE: DNA
<213> ORGANISM: artificial sequence
<220> FEATURE:
<223> OTHER INFORMATION: 12SA

<400> SEQUENCE: 19
aaactgggat tagataccccc actat                                             25

<210> SEQ ID NO 20
<211> LENGTH: 20
<212> TYPE: DNA
<213> ORGANISM: artificial sequence
<220> FEATURE:
<223> OTHER INFORMATION: 12SB

```
<400> SEQUENCE: 20
gagagtgacg ggcggtgtgt                                               20

<210> SEQ ID NO 21
<211> LENGTH: 20
<212> TYPE: DNA
<213> ORGANISM: artificial sequence
<220> FEATURE:
<223> OTHER INFORMATION: 16sarL

<400> SEQUENCE: 21
cgcctgttta ccaaaaacat                                               20

<210> SEQ ID NO 22
<211> LENGTH: 22
<212> TYPE: DNA
<213> ORGANISM: artificial sequence
<220> FEATURE:
<223> OTHER INFORMATION: 16sbrH

<400> SEQUENCE: 22
ccggtctgaa ctcagatcac gt                                            22
```